United States Patent [19]

Milligan

[11] 4,334,988
[45] Jun. 15, 1982

[54] CONTROL OF DIALYSIS AND ULTRAFILTRATION

[75] Inventor: Lee J. Milligan, Englewood, Colo.

[73] Assignee: Hospal Medical Corp., Littleton, Colo.

[21] Appl. No.: 174,856

[22] Filed: Aug. 4, 1980

Related U.S. Application Data

[63] Continuation-in-part of Ser. No. 750,151, Dec. 13, 1976, abandoned, which is a continuation-in-part of Ser. No. 668,420, Mar. 19, 1976, abandoned, and a continuation-in-part of Ser. No. 645,427, Dec. 30, 1975, abandoned.

[51] Int. Cl.$^3$ ............................................. B01D 31/00
[52] U.S. Cl. .................................. 210/87; 210/321.3; 210/416.1
[58] Field of Search .............. 210/637, 89, 646, 321.3, 210/647, 416.1, 744, 746

[56] References Cited

U.S. PATENT DOCUMENTS

| | | | |
|---|---|---|---|
| 3,669,880 | 6/1972 | Marantz et al. | 210/647 X |
| 3,946,731 | 3/1976 | Lichtenstein | 210/321.3 X |
| 4,093,545 | 6/1978 | Cullis | 210/321.3 X |

*Primary Examiner*—Frank A. Spear, Jr.
*Attorney, Agent, or Firm*—Gerald D. Sharkin; Robert S. Honor; Walter F. Jewell

[57] ABSTRACT

Method and apparatus are disclosed for controlling dialysis and ultrafiltration. Precision control over the operation of an artificial kidney (dialyzer), particularly the removal of waste water by ultrafiltration, is achieved by the use of two pumps in the respective paths to and from the artificial kidney. One of the pumps may be operated at constant speed and the other at a variable speed under control from a level sensor at the storage tank, whereby a prescribed rate of ultrafiltration is maintained by a third pump. If desired, the pumps may be operated at complementary speeds so that as the speed of one is increased, the speed of the other is decreased, maintaining a prescribed rate of ultrafiltration by a third pump, under the control of the level sensors at the tank. A further feature provides automatic switching back and forth between two storage tanks of blood cleansing fluid (dialysate) in conjunction with the two pumps in the respective paths to and from the artificial kidney.

The fluid systems are open to the atmosphere rather than being physically enclosed. The maintenance of an essentially constant volume of blood cleansing fluid (dialysate) within the apparatus is dependent upon the use of feedback control of the relative pump speeds derived from a fluid level sensor within the open dialysis liquid tank.

8 Claims, 6 Drawing Figures

CONTROL OF DIALYSIS AND ULTRAFILTRATION

This is a continuation-in-part of co-pending application Ser. No. 750,151, filed Dec. 13, 1976, now abandoned which is in turn a continuation-in-part of applications Ser. No. 645,427 filed Dec. 30, 1975 and Ser. No. 668,420, filed Mar. 19, 1976, both now abandoned.

BACKGROUND OF THE INVENTION

This invention relates to the transfer of solutes and fluids across porous membranes, and more particularly to the precision control of such transfer. These porous membranes are frequently referred to as semipermeable membranes and, as a class, are per se well known in the art.

The transfer of solutes across porous membranes by diffusion is known as dialysis. Ultrafiltration is a separation process in which large molecules or colloidal particles are physically restrained from passing through a porous membrane with the solvent and smaller solutes which do pass through the membrane.

Dialysis and ultrafiltration have important commercial and medicinal applications. They are also widely used in chemical processing to recover and isolate certain constituents. An important medical usage is in the removal of waste materials and fluids when there has been a failure or impairment of function of the human kidney.

The use of dialysis and ultrafiltration in lieu of or in supplement to the kidney function involves the use of an artificial kidney (dialyzer) through which blood from the patient is circulated on one side of a semipermeable membrane, with a cleansing fluid, known as the dialysate, circulating on the other side. Since the process involves the transfer of wastes or excess fluids from the blood to the dialysate, it is known as hemodialysis, with the fluid removed from the blood being known as the ultrafiltrate.

Hemodialysis can take place only as long as there is a concentration gradient between the waste particles in the blood and those present in the dialysate.

In addition to the dialysis, it is important for the ultrafiltration to be controllable with precision. If too little or too much waste fluid is removed from the patient there can be adverse effects such as hypertension or hypotension.

Accordingly, it is an object of the invention to facilitate the control or ultrafiltration. A related object is to facilitate the control of hemodialysis and the removal of waste fluid from the blood by ultrafiltration.

A further object of the invention is to facilitate the change of dialysis liquid without the complete or substantially complete termination of the dialysis process.

SUMMARY OF THE INVENTION

For the purpose of accomplishing the foregoing and related objects, the invention provides for an ultrafiltration control device for controlling ultrafiltration taking place across a semipermeable membrane device, which comprises a dialysis liquid tank for containing dialysis liquid and which is open to the atmosphere, a level sensor for detecting the level of dialysis liquid contained in the open dialysis liquid tank, pump means for pumping dialysis liquid from the dialysis liquid tank to a membrane device and back to the dialysis liquid tank, dialysis liquid withdrawal means in communication with the open dialysis liquid tank for withdrawing determined volumes of dialysis liquid, adjustable dialysis liquid pressure means operative to adjust dialysis liquid pressure in a dialysis liquid line between a point upstream and a point downstream of the membrane device so that the ultrafiltration of liquid being treated is adjusted, and feedback means leading from said level sensor to said adjustable dialysis liquid pressure means for controlling the adjustment of dialysis liquid pressure between said points upstream and downstream of the membrane device in response to and dependently of the level of dialysis liquid sensed by said level sensor in said open dialysis liquid tank.

It will be understood from above that withdrawal of a volume of dialysis liquid from the open dialysis liquid tank by means of said dialysis liquid withdrawal means will tend to decrease the level of liquid in the open dialysis liquid tank with the result that the dialysis liquid pressure means will adjust in response to the level detected so that liquid will enter the dialysis liquid stream across the semipermeable membrane of the device at the same rate as dialysis liquid is withdrawn from the dialysis liquid tank. In this fashion, a constant volume of dialysis liquid is maintained once the system has reached a steady state for a particular rate of withdrawal of dialysis liquid and for a particular membrane device. If the rate of withdrawal of dialysis liquid is adjusted to a new rate, a new steady state will develop.

The adjustable dialysis liquid pressure means operative between a point upstream and a point downstream of the open dialysis liquid tank, i.e. operative to include a semipermeable membrane device, may comprise two separate pumps, one for pumping dialysis liquid from the dialysis liquid tank to the semipermeable membrane device and the other for pumping dialysate from the membrane device back to the tank, the pumping speed of one or both pumps being adjustable to thereby provide means for adjusting dialysis liquid pressure between the two pumps, i.e. between a point upstream and a point downstream of the membrane device. The adjustable dialysis liquid pressure means thus includes the above-mentioned pump means for pumping dialysis liquid from the open dialysis liquid tank to the membrane device and back to the dialysis liquid tank. Conveniently, one of the two pumps may be operated at a constant speed and the other at a variable speed in order to adjust dialysis liquid pressure between the two pumps. Preferably, the dialysis liquid pump upstream of the membrane device is operated at a constant speed so that the amount of dialysis liquid delivered to membrane device is maintained substantially constant, and the other pump downstream of the membrane device is operated at a variable speed dependently of the level of dialysis liquid sensed by the level sensor.

An alternative to the two pump system described above which is contemplated by the present invention is to provide a flow-rate restrictor upstream of the membrane device in place of the upstream pump. It will be appreciated that driving of the pump downstream of the membrane device at a variable speed as described can then achieve a similar control of dialysis liquid pressure in the dialysis liquid line including the membrane device between the flow rate restrictor and the variable speed pump. In this embodiment, the single variable speed pump also constitutes the pump means for pumping dialysis liquid from the dialysis liquid tank to the membrane device and back to the dialysis liquid tank. The flow-rate restrictor can operate in very much the same fashion in regulating pressure as the pump upstream of the membrane device described above in the two pump system. Thus, the flow-rate restrictor is most preferably adjustable between one limit of zero flow and another limit of unrestricted flow.

Where the pump upstream of the membrane device is stationary, or similarly where the flow rate restrictor is set for zero flow, any liquid pumped by the pump downstream of the membrane device must necessarily be replaced by liquid which ultrafiltrates across the semipermeable membrane of the semipermeable membrane device. Where the fluid being treated is blood, this procedure is known as hemofiltration. The device of the present invention is accordingly capable of automatically controlling the rate of ultrafiltration in a situation where dialysis is simultaneously taking place and also controlling the rate of filtration (where no dialysis is taking place) by controlling the rate at which liquid is withdrawn from the open dialysis liquid tank.

In all embodiments of the invention, the dialysis liquid withdrawal means for withdrawing determined volumes of dialysis liquid from the open dialysis liquid tank is most suitably an occlusive or volumetric pump capable of providing an accurate reading of the rate of withdrawal which can be integrated to reflect a total of the amount of liquid withdrawn.

Similarly, it is most preferable that pumps employed upstream and downstream of the membrane device are occlusive, although this is not essential since the variable speed pump will necesarily be driven at that rate which is necessary to develop that pressure between said points upstream and downstream of the membrane device which will lead to filtration or ultrafiltration across the membrane taking place at the rate at which liquid is withdrawn by the dialysis liquid withdrawal means. It will be appreciated from above that this aspect of the invention is achieved by driving of the variable speed pump at a rate which is dependent on the level of dialysis liquid sensed by the level sensor in the open dialysis liquid tank.

So that spent dialysis liquid (dialysate) can be replenished with freshly dialysis liquid in the tank without discontinuing the dialysis process, a bypass circuit and appropriate valves may be provided to enable dialysis liquid to continue to flow through the membrane device. Alternatively or additionally, two dialysis liquid tanks may be provided which may be alternately switched into the dialysis liquid circuit so that while one tank is delivering dialysis liquid to the membrane device, the other may be replenished with fresh dialysis liquid.

As mentioned above, dialysis liquid is delivered from the dialysis liquid tank to the membrane device and then back to the dialysis liquid tank. This arrangement enables control over the total volume comprised in the entire system and which is maintained constant for any particular ultrafiltration rate. A dividing wall, for example in the form of a flexible membrane, may be provided for separating fresh dialysis liquid from spent dialysis liquid (dialysate). However, a significant amount of mixture can be avoided by constructing a major portion of the volume of the dialysis liquid tank in tubular form which is conveniently coiled so that mixture of spent and fresh dialysis liquid is limited to the relatively small interface region between the two liquids.

The ultrafiltration control device of the present invention involves the important concept that the parameter to be controlled is not essentially transmembrane pressure but rather actual ultrafiltration volume or ultrafiltration rate. There are a variety of devices involving monitoring of pressures in an effort to establish a determined ultrafiltration volume or ultrafiltration rate. Such an approach, however, can only possess a limited accuracy in that the effect of transmembrane pressure on ultrafiltration rate is dependent not only on the transmembrane pressure but also on the permeability properties of the membrane in a membrane device, which can change not only from one device to another but also during a period of use of the membrane device.

The first disclosure of the above concept is comprised in U.S. Pat. No. 3,939,069 assigned to Rhone-Poulenc-Textile, Paris, in which a constant volume system closed to the atmosphere defines the circuit in which dialysis liquid is circulated over a semipermeable membrane device. Predetermined amounts of dialysis liquid are withdrawn by pumping from said constant volume closed system as a result of which the ultrafiltration volume or rate across the semipermeable membrane is necessarily the same as the predetermined amounts of dialysis liquid withdrawn from the constant volume closed system. In other words, the transmembrane pressure applied is dependent on the volume or rate of withdrawal of dialysis liquid from the constant volume closed system.

Another dialysis liquid system closed to the atmosphere is one in which two interdependent volumetric pumps deliver dialysis liquid to and from a semipermeable membrane device, the ratio of volumes of dialysis liquid delivered to and removed from the membrane device being adjustable.

In each of the above systems the entire dialysis liquid circuit is necessarily closed to the atmospheres so that dialysis liquid pressure and hence transmembrane pressure will be a function of volume of dialysis liquid removed from the closed system. In the case of the two interdependent volumetric pumps, the volume of dialysis liquid removed from the closed system corresponds to the increase in volume of the volumetric pump downstream of the membrane device over that of the volumetric pump upstream of the membrane device.

The above systems, by virtue of the fact that the dialysis liquid circuit will in general be below atmospheric pressure and will also not be capable of distinguishing volumes of air or air bubbles over volume of dialysis liquid, accompanied by the fact that any air vent can only be localized to a small section of the dialysis liquid circuit, have limitations as to accuracy of ultrafiltration measurements by volumetric pump means. Also, as already indicated, deaerating of dialysis liquid in systems closed to the atmosphere can only be incompletely controlled and may be inadequate to avoid bubbles entering the dialysis liquid side of a membrane device.

In contrast to above, the ultrafiltration control device of the present invention involves a dialysis liquid circuit in which a major component thereof is open to the atmosphere, which allows air or vapour bubbles entrained or developed as a result of heating or pressure reduction to escape readily.

The present invention achieves the advantages of both volumetric control of ultrafiltration and freedom from volumetric errors resulting from the formation of air bubbles within the dialysis liquid.

DESCRIPTION OF THE DRAWINGS

Other aspects and features of the invention will become even more apparent after considering several illustrative embodiments, taken in conjunction with the accompanying drawings in which.

DETAILED DESCRIPTION

Figures 1, 2:
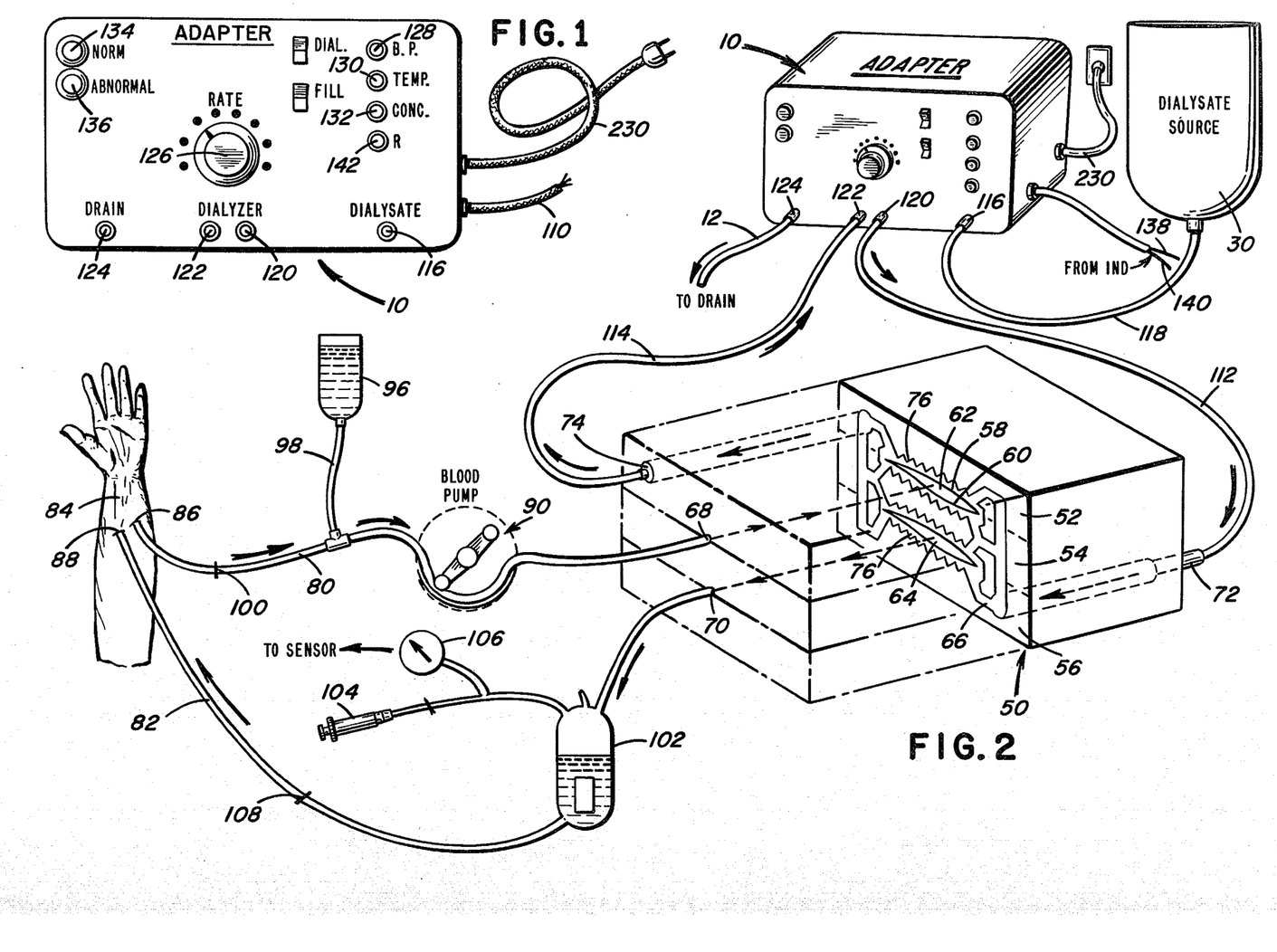
FIG. 1 is a front view of a dialysis and ultrafiltration control unit in accordance with one embodiment of the invention.
FIG. 2 is a perspective view of a dialysis and ultrafiltration system employing the dialysis and ultrafiltration control unit of FIG. 1.

Turning to the drawings, and especially the embodiment shown in FIGS. 1 to 4, a dialysis and ultrafiltration control unit 10 of FIG. 1 is shown connected for control of an illustrative hemodialyzer 50 in FIG. 2.

It will be understood that while the invention is being illustrated for hemodialysis (i.e. removal of waste products from the blood) and ultrafiltration (i.e. removal of waste fluid), it applies generally to all forms of dialysis and ultrafiltration in which substances in solution are separated by a semipermeable membrane of a natural or synthetic origin, such as cellulose, cellophane, parchment, acrylonitrile hompolymer or copolymers, polycarbonate polymers and copolymers, etc., through which solutes and colloidal particles may diffuse.

Thus, dialysis can be used in manufacturing processes for the recovery of reagents, catalysts and process chemicals. One such example is the recovery of sodium hydroxide in the manufacture of viscose.

The dialysis and ultrafiltration control unit 10 is used as shown in FIG. 2 to regulate the flow of dialysate that originates at a source 30 and is pumped to the dialyzer 50 in a manner that achieves precision control of ultrafiltration, which is the removal of waste fluid from the blood being dialyzed, and the discharge of the waste by a drain line 12.

The dialyzer 50 of FIG. 2 is a so-called parallel-plate artificial kidney, but it will be understood that the invention may be used with other kinds of artificial kidneys and dialyzers.

The particular parallel-plate kidney 50 of FIG. 2 is typically formed of polypropylene frames 52, 54, 56, with two thin membranes 58 and 60 and porous regenerated cellulose for each blood compartment 62 and 64. Suitable regenerated cellulose membranes for hemodialysis and ultrafiltration are sold and marketed under the name "Cuprophan" by the Enka Glanzstoff Company.

A dialysate compartment 66 is located between the frames 52, 54 and 56, and the blood compartments 62 and 64. Access to the blood compartments 62 and 64 from the patient being dialyzed is at blood ports 68 and 70. The dialysate pumped from the control unit 10 enters at a dialysate port 72 and leaves at a port 74, after flowing in longitudinal grooves 74 of the dialyzer frames counter to the flow of the blood.

The regenerated cellulose membranes 58 and 60 in the dialyzer 50 keep the blood separated from the dialysate. The membranes 58 and 60 have minute pores or micropores with mean diameters of the order of about $1\mu$ more or less.

Waste products in the blood pass through the membranes 58 and 60 by virtue of a concentration gradient. When the dialysate is first circulated, it is free of waste products. Consequently those waste products having a mean diameter less than that of the pores in the membranes 58 and 60 will pass through from the blood into the dialysate so long as there is a concentration difference of the waste materials on both sides of the membrane.

In addition, where the pressure on the blood side is sufficiently greater than the pressure on the dialysate side, i.e. sufficient to compensate for the inherent osmotic pressure, fluid will pass through membranes 58 and 60 from the blood into the dialysate. This process is known as ultrafiltration.

The dialysis and ultrafiltration control unit 10 provides a convenient way of replacing the waste dialysate with a fresh supply while minimizing interruption of the dialysis process. In addition, the removal of waste water by ultrafiltration is controlled with precision.

Access to a patient in need of dialysis, for example, because of failure or impairment of the kidney function, is shown in FIG. 2 to be by blood inflow and outflow lines 80 and 82 between the patient and the dialyzer. The lines are connected to the patient at a convenient place, typically the arm 84, by cannulae 86 and 88, inserted into an artery and a vein respectively.

The exemplary dialyzer 50 shown in FIG. 2 is of a low resistance type, so that the patient's blood pressure is generally sufficient to maintain a suitable flow of blood into and through the dialyzer 50. The resulting flow rate is generally from 150 to 200 milliliters per minute. When it is desired to increase the rate to the order of about 300 milliliters per minute, a blood pump 90 is employed. The blood pump 90 may be of any conventional type.

Upstream of the blood pump, 90, on the arterial side, there is a container 96 of priming solution, usually comprising a conventional saline solution containing a small amount of sodium heparin. This is used to fill the line before it is attached to the patient at 84 via 86 and 88. During dialysis the container 96 is closed off by a clamp 98 and a clamp 100 is open. At the end of dialysis, the blood in the line between the patient and the dialyzer is reinfused into the patient by closing clamp 100 and opening the clamp 98 to allow the saline and the heparin solution to force the blood in the line back into the patient.

On the venous side of the system there is a bubble catcher 102 communicating with a syringe 104 and a blood pressure indicator 106. When a clamp 108 on the venous side is opened, the syringe 104 can be used to control the level of blood in the bubble catcher 102 and to remove air. The blood pressure is monitored by the indicator 106 which is connected by a lead (not shown) to a sensor cable 110 of the control unit 10.

Once the dialyzer 50 is connected to the patient, the control unit 10 is connected to the dialyzer by lines 112 and 114 to enable pumping of the dialysate to and from the dialyzer, respectively.

The dialysate is supplied to the control unit 10 via an input port 116 over a line 118 from the source 30. It will be understood that the flow and distribution of dialysate within the control unit 10 are through and via various lines and tanks, etc., as and in the manner shown schematically in the flow sheet of FIG. 3 as described more fully hereinafter.

The dialysate is pumped to the dialyzer 50 from an exit port 120 via line 112 (FIG. 2) and returned at an entry port 122 via line 114. The volumetric equivalent of the waste fluid extracted from the blood by ultrafiltration and carried by the returning dialysate is discharged over a drain line 12 from a drain port 124.

The rate of ultrafiltration is controlled by the setting of a dial 126 (FIG. 1).

The conditions of various monitors associated with the dialysis are indicated on the unit 10 by warning lights 128, 130, 132, 134 and 136. Thus, any abnormal blood pressure condition is detected by a sensor that responds to the indicator 106 and is connected to the warning light 128. There is also a monitoring of dialysate temperature by a thermostatic probe 138 at the output of the dialysate source 30 and a corresponding warning light 130. Another probe 140 at the output of the dialysate source 30 measures the electrical conductivity of the dialysate and indicates any abnormal measurement at a corresponding third warning light 132.

If all monitored conditions are satisfactory this is indicated by the "NORM" light 134; otherwise there is a warning indication by the "ABNORMAL" light 136. In addition, upon occurrence of an abnormal condition, a reset indicator and switch 142 is activated. The unit 10 can then be reset by depressing the switch 142.

It will be understood that the monitors 128, 130, 132, 134 and 136 are merely illustrative and that other monitors may be provided as well, for example, to measure dialysate flow by a rotameter (variable-area flow tube) or other flowmeter; dialysate pressure by a manometer or other pressure gauge; and blood leaks into the dialysate effluent or line 144 by a photoelectric pickup to detect color change.

Figures 3, 4:
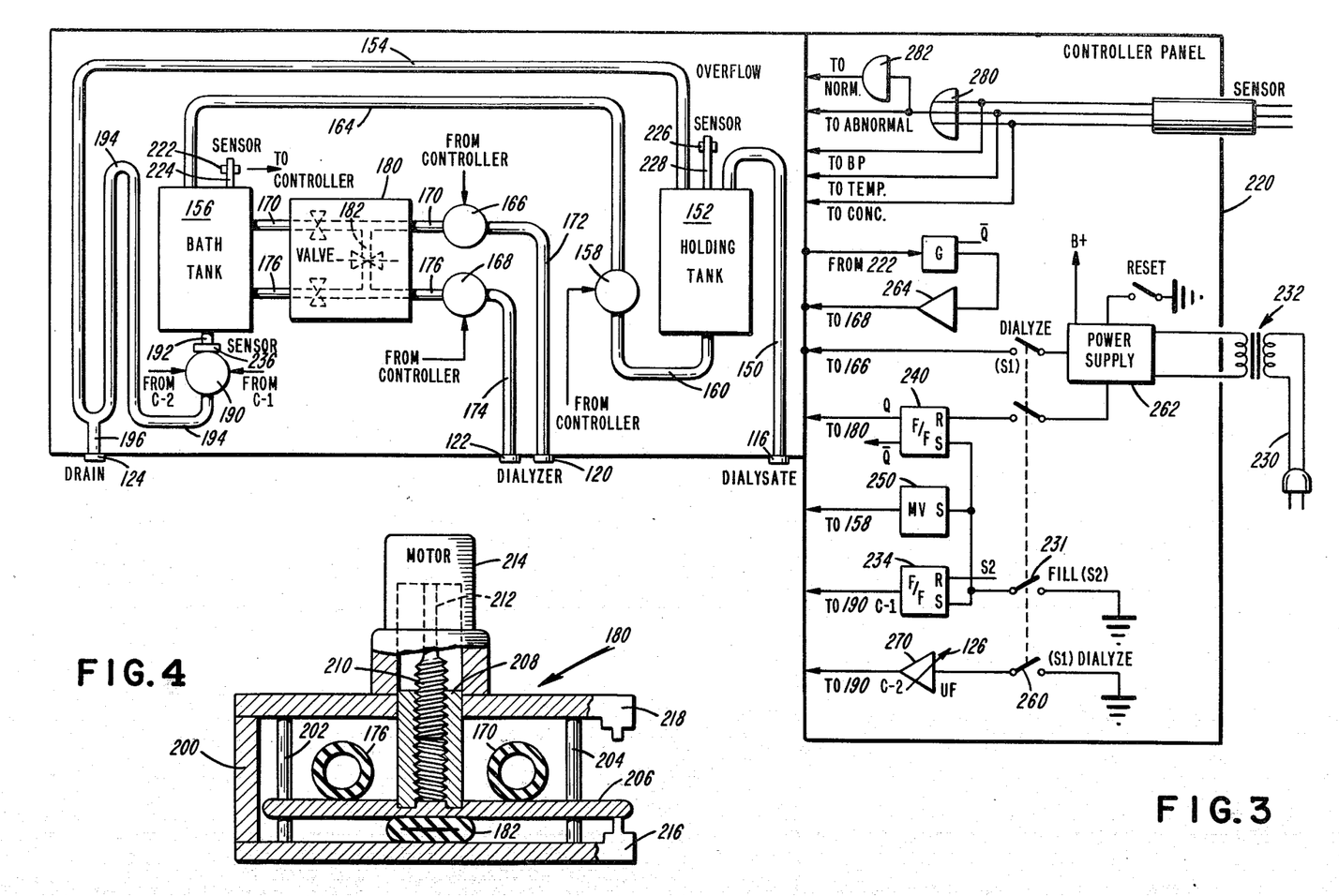
FIG. 3 is a schematic diagram of the dialysis and ultrafiltration control unit of FIGS. 1 and 2, including illustrative control circuitry.
FIG. 4 is a view, partially in section, of a control valve in accordance with the invention for the dialysis and ultrafiltration control unit of FIGS. 1 and 2.

The components that provide precision control over dialysis and ultrafiltration by the unit 10 are shown schematically in FIG. 3.

Dialysate from the source 30 (FIG. 2) enters at the port 116 over a line 150 (FIG. 3) to a holding tank 152. Filling takes place until there is overflow on a drain line 154, with the overflow exiting at the drain port 124. Filling can take place by pumping from the dialysate source 30, but if desired one may use gravity flow by locating the source 30 above the unit 10 and a suitable clamp (not shown) on the external fill line 118 (FIG. 2).

This overflow fill technique assures that a sufficient amount of dialysate is in the holding tank 152. Once the holding tank 152 is filled, its contents may be readily pumped to a dialysis liquid bath tank 156 by a pump 158 (or by any equivalent means such as a valve controlling gravity feed) which draws the dialysate through a supply line 160 into the pump 158 and then discharges it into the bath tank 156 through fill line 164.

Once there is dialysate in the bath tank 156, it can be circulated to and from the artificial kidney 50 (FIG. 2) via ports 120 and 122 by pumps 166 and 168. Outflow takes place over line 170 to the pump 166 and then from the pump 166 over line 172 to the artificial kidney or dialyzer 50 via port 120.

The dialysate returns from the artificial kidney via port 122 and flows over a line 174 into the pump 168, then out of the pump 168 via line 176 and into the bath tank 156, thus completing the cycle.

The foregoing flow can take place only if a valve 180 located between the bath tank 156 and the pumps 166 and 168 is open with respect to the lines 170 and 176. When the bath tank 156 is being filled, the valve 180 is quickly closed so that no flow can take place between the bath tank 156 and the dialyzer 50. However, any prior flow of dialysate to the dialyzer continues to take place via a bypass line 182.

When ultrafiltration is to take place, or the bath tank 156 is to be emptied, a pump 190 is operated to drain fluid from the tank 156 via line 192 and expel it via line 194 into the drain line 196, port 124 and drain line 12.

Details of a suitable valve 180 are shown in FIG. 4. The valve mechanism includes a frame 200 which mounts guide bars 202 and 204 for a pressure plate 206. The plate 206 contains appropriate bearing apertures (not shown) to permit it to slide along the guide bars 202 and 204. The plate 206 is also attached to a nut 208 which is engaged by an endless screw 210. The latter is an extension of the armature shaft 212 of a drive motor 214.

When the motor 214 is actuated from a controller panel 220 described below, the plate 206 is quickly driven up or down until a limit switch 216 or 218 is contacted to turn off motor. When the plate 206 is in its down position as shown, the by-pass line 182 is closed and the dialyzer supply lines 170 and 176 are open. Conversely, when the plate 206 is in its up position, the by-pass line 182 is open and the lines 170 and 176 are closed.

The various valves, pumps, etc., may be actuated and controlled in any desired manner. A particularly desirable arrangement, however, is as follows:

The necessary operations are controlled by suitable circuitry mounted on a controller panel 220 and by a level sensor 222, on a vent tube 224 of the bath tank 156. A similar level sensor 226 on a vent tube 228 can be used with the holding tank 152. Voltage at the desired level is supplied from the cable 230 by a transformer 232. After the dialysate has filled the holding tank 152, the FILL switch 231, 260 for the bath tank 156 is closed. This sets a flip-flop 234 to operate the pump 190.

Setting of a flip-flop produces a high level voltage on a primary output lead until the flip-flop is reset. The pump 190 drains the bath tank 156 until a sensor 236 associated with the pump 190 detects the absence of any further fluid and applies a signal to the reset terminal R of the flip-flop 234.

For initial operation, the bath tank 156 will be empty, so that the sensor 236 operates immediately to terminate the operation of the pump 190.

A second flip-flop 240 simultaneously responds to the closure of the fill switch 231 to operate the valve 180, closing the lines 170 and 176 between the valve 180 and the bath tank 156, and opening the by-pass line 182. This has no effect on the initial operation, but in subsequent operations where the bath tank 156 is drained, this permits continued flow of the dialysate in a separate loop to and from the artificial kidney 50 until the replacement solution in the bath tank 156 is ready to be used.

After drainage of the bath tank 156, a one-shot multivibrator 250 operates for a time constant interval to operate the pump 158 and pump fresh dialysate from the holding tank 152 into the bath tank 156. The one-shot multivibrator is of standard design with a built-in time delay line at its set terminal S. At the end of the delay interval the multivibrator 250 operates for a prescribed discharge interval determined in standard fashion by a resistance-capacitance network.

Once the new dialysate reaches the preset reference level in the bath tank 156 (which is measured by the level sensor 222) this then stops pump 158 and dialysate may then be circulated to the artificial kidney by operating the dialyze switch 260. This resets the flip-flop 240 to reverse the closure of the valve 180 so that now the lines 170 and 176 are open and the by-pass line 182 is closed.

The closure of the switch 260 also applies a constant bias voltage from the power supply 262 to the constant speed pump 166, while the variable speed pump 168 is supplied with a voltage from an amplifier 264 according to the level sensed by the sensor 222. While the bath tank 156 is being drained, the sensor voltage 222 is prevented from affecting the amplifier 264 by a gate $\underline{G}$ which is controlled from the complementary output $\overline{Q}$ of the flip-flop 240. As a result, pump 166 assures circulation of dialysate in the separate loop formed by the bypass line 182 and the connections to the dialyzer. In order to assure that the inactive pump 168 (i.e., inactive during the filling of the bath tank 156) will not interfere with the flow of the dialysate in the aforesaid separate loop, it is desirable for the pump 168 to have an inernal bypass.

The dialyze switch 260 also operates the ultrafiltration control amplifier 270 which applies an appropriate voltage to the occlusive drain pump 190 in accordance with the desired rate of ultrafiltration set by the control knob 126 (FIG. 1).

When the ultrafiltration rate is set for zero, no waste fluid is to be withdrawn via the artificial kidney 50 and the feedback amplifier 264 adjusts the speed of the pump 168 so that the pressure of the dialysate in the artificial kidney is set accordingly. Consequently no waste fluid from the blood can flow into the dialysate.

As the ultrafiltration rate is set above zero on the control knob 126, the pump 190 operates and the level of fluid in the sensor 222 drops, causing an increase in the voltage applied to the amplifier 264 and increasing the speed of the pump 168 relative to the constant speed of the pump 166. The result is reduction in the pressure of the dialysate in the dialysate compartment of the dialyzer, that is to say, an augmentation of the transmembrane pressure, so that waste fluid passes from the patient's blood into the dialysate. Thus the volume of the fluid removed from the dialysate circuit is replaced and the level of fluid in the sensor 222 rises up. As a consequence, dialysate is discharged at a controlled rate in the drain via port 124.

The rate of ultrafiltration established by the control knob 126 can be changed by increasing the drainage rate. A separate discharge port (not shown) can be provided for the ultrafiltrate together with auxiliary pump and monitoring circuitry. If desired, the same pump 190 can be employed for both purposes.

By contrast with the prior art, the use of the two pumps 166 and 168 to feed the dialyzer, in conjunction with the sensing of the level in the bath tank 156 by the sensor 222, permits precision control over ultrafiltration. The system is self-adjusting, regardless of conditions such as, for example, change in blood pressure or pressure drop in the fluid circuits.

In addition, the provision of the valve 180 with by-pass line 182 permits the dialysis process to be maintained while the bath tank 156 is being supplied with fresh dialysate, thereby minimizing interruptions to the dialysis treatment of the patient.

It will be understood that the circuitry of the controller panel has been expressly simplified for purposes of explanation and that the various operations described above can be performed in a wide variety of ways.

The controller panel 220 also includes illustrative circuitry for the indicators 128, 130, 132, 134 and 136 (FIG. 1). As noted above the sensors supply signals to the panel 220 over a cable 110. The individual lines in the cable 110 are connected to respective indicators 128, 130 and 132. In addition, lines are included that go to an OR gate 280 so that if any abnormal condition is indicated there will also be an input to the indicator 136; otherwise, because of the NOT gate 282 the indicator 134 will be illuminated to show that conditions are "normal".

The OR gate 280 and the NOT gate 282, which can be an ordinary inverting amplifier, are standard electronic components, along with the flip-flops 234 and 340, and the delay one-shot multivibrators 250. Moreover, instead of discrete components, the controller panel 220 may employ integrated circuit chips to consolidate as many electronic functions as desired on one circuit chip. In fact, the flip-flops, for example, are generally individual circuit chips.

Suitable pump units 166 and 168 are provided by Model 08-33-103 gear pumps manufactured by the Micromite Company of California. The motor portion operates at a speed determined by the voltage input and has a magnet drive for the pump portion. The pump 166 may be provided with a suitable by-pass. However, either or both pumps 166 and 168 may be of the centrifugal type, in which case no pump by-pass is necessary. The voltage supplied to the pump 166 may be regulated in accordance with the load to maintain constant speed, or the motor portion may be of the synchronous type to assure constancy of speed regardless of load.

The pump 158 may be of the regular centrifugal variety, while the pump 190 is occlusive, i.e., of the positive drive type for example as provided by a piston pump.

Level sensor 222 is, illustratively, a linear voltage differential transformer with a movable core that is positioned by a float responsive to the level of the liquid in the vent 224 to control the coupling to the transformer.

Other suitable kinds of sensors may be employed, such as optical, capacitive or a float provided with various integrated circuitry for bringing about a linear voltage response.

The system is atmospheric, i.e., open to the atmosphere rather than being completely closed. Access to the atmosphere is provided via the vent tubes 224 and/or 228 (FIG. 3). In this way bubbles of gas, such as air, that otherwise might enter and remain in the circulating dialysate and disrupt the efficient functioning of the dialyzer 50 are readily eliminated from the system.

Figure 5:
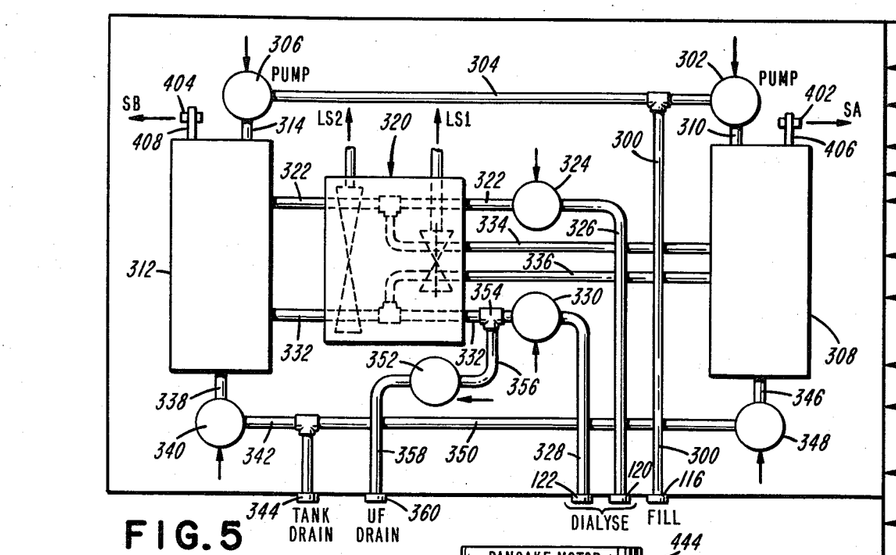
FIG. 5 is a schematic diagram of the dialysis and ultrafiltration control unit, including illustrative control circuitry in accordance with another embodiment of the invention.
Figure 6:
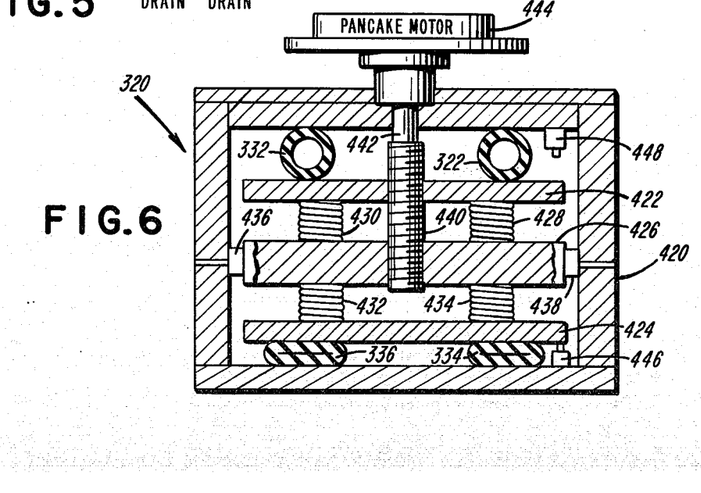
FIG. 6 is a view, partially in section, of a control valve in accordance with the embodiment of the invention shown in FIG. 5.

A second embodiment of the invention is illustrated in FIGS. 5 and 6. This embodiment is generally similar in overall function and mode of operation to the of FIGS. 1 to 4, and therefore in the interest of brevity only those components thereof that differ from those already described in connection with FIGS. 1 to 4 will be described in detail. Like reference numerals will be employed for elements having like functions.

To state the difference broadly, however, in this second embodiment of the invention, precision control over the operation of the artificial kidney, and particularly the removal of waste water by ultrafiltration, is achieved by the automatic switching back and forth between two storage tanks for the dialysate in conjunction with two pumps in the respective paths to and from the artificial kidney. These two pumps operate at complementary speeds, thus maintaining constant flow through the artificial kidney, while at the same time maintaining a prescribed rate of ultrafiltration by a third pump under the control of level sensors associated with the tanks. Separate drains are provided instead of the single drain of the first embodiment (124 of FIGS. 1 and 3 and 12 of FIG. 2).

In this second embodiment, two tanks for dialysate are provided, but in this instance instead of one tank being a "holding" tank for the other as in the first embodiment, the two tanks are so constructed and arranged in the system that they can be automatically switched in and out of the dialysate circuit as more fully described hereinafter, thereby making it possible to carry out the dialysis on the patient with a minimum of interruption of the actual dialysis process.

Dialysate from the source 30 enters at the port 116 and is carried by gravity or pumped via line 300 to a valve 302 and also by a line 304 to a valve 306 (FIG. 5). When the valve 302 is opened, dialysate enters a tank 308 through line 310. Similarly, when the valve 306 is opened, dialysate enters a tank 312 through line 314.

Once the tanks 308 and 312 are filled, dialysate can be pumped from either, according to the setting of the valve 320. Assuming that the valve 320 is set according to FIG. 6, below, dialysate can flow from tank 312 via line 322 into the pump 324 and from the pump 324 along the line 326 to the dialyzer port 120.

The dialysate returns from the dialyzer via the port 122 via line 328 into the pump 330. The dialysate is then extracted by this pump 330 into the tank 312 through the open side of the valve 320 via a line 332.

When the system is ready for a fresh supply of dialysate, the valve 320 closes with respect to tank 312 and opens with respect to tank 308. When this happens, dialysate is drawn along a line 334 which loops through the bottom portion of the valve 320 to a junction with line 322 and then into the pump 324. From the pump 324 the dialysate moves along the line 326, as before, and returns on the line 328 into the pump 330. It then flows along line 332 to a junction with line 336 that, like line 334, loops through the valve 320 back to the tank 308.

While fresh dialysate is being drawn from the tank 308, the spent dialysate in tank 312 is drawn along a line 338 through a valve or pump 340 and expelled by gravity or pressure into a drain line 342 and drain 344. Similarly, while fresh dialysate is being drawn from tank 312, the spent dialysate in tank 308 is drawn along a line 346 through a valve or pump 348 and expelled by gravity or pressure into a drain line 350 and drain 344.

When ultrafiltration is to take place, a pump 352 is operated to draw returning dialysate from the return side of the pump 330. As indicated in FIG. 5, this is accomplished by a junction 354 in the line 332 between the pump 330 and the valve 320. Any comparable arrangement could be used instead. From the junction 354 the dialysate is drawn through a line 356 and expelled via pump 352 and expelled via line 358 into an exit port 360. In order to avoid ultrafiltrate mixing with tank drainage, separate drain ports 344 and 360 are provided. The ultrafiltrate from the exit port 360 can be measured to confirm the proper operation of the ultrafiltration controller.

The foregoing operations are controlled by circuitry mounted on a controller panel 400 and by level sensors 402 and 404 mounted on vent tubes 406 and 408 of the tanks 308 and 312, respectively. As in the first embodiment described above, the vent tubes 406 and 408 are open to the atmosphere.

Details of a suitable valve 320 are shown in FIG. 6. The valve mechanism includes a frame 420 with pressure plates 422 and 424 that are able to engage the lines 322 and 332, and the lines 334 and 336. The pressure plates are driven by a drive plate 426 through coil springs 428, 430, 432 and 434. The drive plate 426 is guided by rollers 436 and 438 and is threadedly engaged by a shaft 440. The latter is an extension of an armature shaft 442 of a drive motor 444.

When the motor 444 is operated from the controller panel 400 (by the "V" lines), the plate 426 is quickly driven up or down until a limit switch 446 or 448 is contacted to turn-off the motor 444, when the plate 426 is in the position shown in FIG. 6, the lines 334 and 336 are closed by the pressure transmitted to the plate 424 through the springs 432 and 434, the lines 322 and 332 are open, and a signal is available from the limit switch 446. Conversely, when the plate 426 is drawn upwardly by the threaded shaft 440, pressure is transmitted through the springs 428 and 430 until the plate 422 contacts the upper limit switch 448 and closes the lines 322 and 332, opening the lines 334 and 336.

The motor 444 is advantageously of the Model 12F so-called pancake type available from the Printed Motors Division of Kollmorgen Corp. of Glen Cove, N.Y.

Voltage at the desired level for this second embodiment is supplied from the cable 230 by a transformer 232.

An illustrative detailed operation of the control unit 10 for the second embodiment of FIG. 5 is as indicated by FIG. 5. The unit 10 is set into operation with the dialysate source 30 connected at the port 116, by closure of the switch 460. This sets a flip-flop 462 which activates pump or opens the valve 302 until the appropriate level is detected by the level sensor 402, which resets the flip-flop 462 and shuts the valve 302. A flip-flop is a two state electronic device with one output at a high level or a low level in accordance with the signal at a set terminal S and a reset terminal R.

Once the tank 308 is full, it can be used for dialysis by the pumps 324 and 330, provided that the lines 334 and 336 are open (i.e., the limit switch 448 of the valve 320 is on and the lines 322 and 332 are closed (FIG. 6)). With the limit switch 448 on and tank 308 full (so that a control signal from the level sensor 402 appears), an AND gate 463 is operated. This operates a gate 464 to permit the level of the signal from the sensor 402 to control the pump amplifiers 466 and 468. This begins the dialysis flow from tank 308 as described above.

While the first tank 308 is dialyzing i.e., is connected into the dialysis liquid circuit, the second tank 312 is filling, as controlled by the $\bar{Q}$ output of the flip-flop 470 operated by the AND gate. The $\bar{Q}$ output opens valve 306 and causes the second tank 312 to begin filling.

If the limit switch had not been in the correct position for the foregoing operational sequence, it would have been placed in operating condition by a signal from the level sensor 402 after appropriate delay in a delay unit 472 to permit closure of a NOT gate 474 if no operation of the valve 320 to change the limit switch responses is indicated.

The $\overline{Q}$ output of the flip-flop 470 also opens the drain valve 348 for timed interval through a one-shot multivibrator 476, as well as the valve 320 after a delay interval provided by a delay unit 478. This changes the setting of the valve 320 to transfer quickly dialysis to the second tank 312 when it is filled to the appropriate level indicated by the sensor 404, which acts with the signal from the first limit switch 446 at an AND gate 450 to operate the gate 482 for control of the pump amplifiers 466 and 468.

In the meantime the $\overline{Q}$ output of the flip-flop 470 fills the first tank 308 and opens the valve 340 by a one-shot multivibrator 482 through a delay unit 484.

As a result, the control unit 10 automatically switches the tanks 308 and 312 between dialysis and fill cycles. Appropriate time delay periods can be provided as desired.

In addition, the control unit 10 provides precision control over ultrafiltration. The ultrafiltrate is drawn by the occlusive pump 352 which is operated by a variable amplifier 486, the setting of which is determined by the control knob 126.

When the ultrafiltration rate is set for zero, no waste fluid is to be drawn from the artificial kidney 50 and the amplifiers 466 and 468 adjust the speeds of the pumps 324 and 330 so that the pressure of the dialysate in the artificial kidney is set accordingly. Consequently no waste fluid from the blood can flow into the dialysate.

As the ultrafiltration rate is set above zero, the pump 352 operates and the level of fluid in the sensor 402 or 404 (depending on which tank is dialyzing at the moment) drops, causing an increase in the voltage of the amplifier 468 and a corresponding decrease in the voltage of the amplifier 466. In effect, the amplifiers 466 and 468 act as an operational amplifier with cross-coupled input I and negative input NI terminal. A constant amplitude reference voltage is provided by the power supply 488.

As a result, any increase in speed of the pump 330 is matched by a decrease in the speed of the pump 324. Conversely, any decrease in the speed of the pump 330 is matched by an increase in the speed of the pump 324. Consequently, the dialysate flow rate is maintained substantially constant despite any change in the rate of ultrafiltration. The pumps 330 and 324 provide negative pressure in the artificial kidney, with the pump 330 operating faster than the pump 324.

The rate of ultrafiltration established by the control knob 126 can be checked by measuring the collected ultrafiltrate.

The use of the two pumps 324 and 330 to feed the dialyzer 50, in conjunction with the sensing of the level in the dialyzing tank 308 or the tank 312 by the sensor 402 or 404 (respectively) permits precision control over ultrafiltration. The system is self-adjusting, regardless of ambient conditions, to the desired operation.

It will be understood that the circuitry of the controller panel 400 has been expressly simplified for purposes of explanation and that the various operations described above can be performed in a wide variety of ways.

The controller panel 400 also includes illustrative circuitry for the indicators 128, 130, 132, 134 and 136 (FIG. 1). As noted above, the sensors supply signals to the controller panel 400 over a cable 110. The individual lines in the cable are connected to respective indicators 128, 130 and 132. In addition, the lines go to an OR gate 490 so that if any abnormal condition is indicated there will also be an input to the indicator 136; otherwise, because of the NOT gate 464 the indicator 134 will be illuminated to show that conditions are "normal".

The AND gate 463 and the NOT gate 474, which can be an ordinary inverting amplifier, are standard electronic components, along with the flip-flops 462 and 470, and the delay one-shot multivibrator 476. Moreover, instead of discrete components, the controller panel 400 may employ integrated circuit chips to consolidate as many electronic functions as desired on one circuit chip. In fact, the flip-flops, for example, are generally individual circuit chips.

Suitable pump units 324 and 330 are provided by the Model 08-33-103 gear pumps manufactured by the Micromite Company of California. The motor portion operates at a speed determined by the voltage input and has a magnet drive for the pump portion.

The pump 352 is of the positive displacement of occlusive type, whereas valves or pumps, if desired, 302, 306, 340 and 348 are occlusive. Such a pump is of the positive drive or positive displacement type, as provided by e.g. a piston pump.

The level sensors 402 and 404 illustratively are linear voltage differential transformers with a movable core that are positioned by the level of the liquid in the vent tubes with which they are associated to control the coupling to each transformer. As indicated above, the vent tubes are open to the atmosphere.

While various aspects of the invention have been set forth in the drawings and specification, it is to be understood that the foregoing detailed description is for illustration only and that various changes in parts, as well as the substitution of equivalents for what has been shown and described, may be made without departing from the spirit and scope of the invention as set forth in the appended claims.

What is claimed is:

1. A dialysis and ultrafiltration control system for controlling ultrafiltration taking place across a semipermeable membrane device, which comprises a dialysis liquid tank for containing dialysis liquid and which is open to the atmosphere, a level sensor for detecting the level of dialysis liquid contained in the open dialysis liquid tank, dialysis liquid withdrawal means in communication with the open dialysis liquid tank for withdrawing determined volumes of dialysis liquid, means for effecting the circulation of the stream of dialysis liquid which means includes two positive-flow pumps, one disposed upstream and the other downstream of the dialyzer so that the ultrafiltration of liquid being treated is adjusted, and feedback means leading from said level sensor to said positive-flow pumps, wherein the means for controlling ultrafiltration constitutes controlling the operation of the two pumps in relation to each other in response to the level of dialysis liquid sensed in the tank in such manner as to maintain a substantially constant level of dialysis liquid in said tank at a determined rate of withdrawal of dialysis liquid.

2. A dialysis and ultrafiltration control system as defined in claim 1, wherein one of the two positive-flow pumps is driven by a constant speed motor and the other is driven by a variable speed motor.

3. A dialysis and ultrafiltration control system as defined in claim 2, where the pump driven by the constant speed motor is disposed upstream of the dialyzer and the other pump is disposed downstream of the dialyzer, and means for increasing the speed of the variable speed motor when the level of dialysis liquid in the tank decreases and vice versa.

4. A dialysis and ultrafiltration control system as defined in claim 2, where the pump driven by the constant speed motor is disposed downstream of the dialyzer and the other pump is disposed upstream of the dialyzer, and means for decreasing the speed of the variable speed motor when the level of dialysis liquid in the tank increases and vice versa.

5. A dialysis and ultrafiltration control system as defined in claim 1, wherein each of the two pumps is driven by a variable speed motor.

6. A dialysis and ultrafiltration control system as defined in claim 5, including means for increasing the speed of the variable speed motor driving the downstream pump when the level of dialysis liquid in the tank decreases and vice versa.

7. A dialysis and ultrafiltration control system as defined in claim 5, including means for decreasing the speed of the variable speed motor driving the upstream pump when the level of dialysis liquid in the tank increases and vice versa.

8. A dialysis and ultrafiltration control system as defined in claim 1, including means for monitoring a substantially constant rate of flow of dialysis liquid in the dialyzer.

* * * * *